(12) United States Patent
    Gifford et al.

(10) Patent No.: US 9,302,125 B2
(45) Date of Patent: Apr. 5, 2016

(54) METHODS AND APPARATUS FOR NON-INVASIVELY TREATING ATRIAL FIBRILLATION USING HIGH INTENSITY FOCUSED ULTRASOUND

(75) Inventors: Hanson S. Gifford, Woodside, CA (US); Mark E. Deem, Mountain View, CA (US)

(73) Assignee: The Foundry, LLC, Menlo Park, CA (US)

( * ) Notice: Subject to any disclaimer, the term of this patent is extended or adjusted under 35 U.S.C. 154(b) by 2349 days.

(21) Appl. No.: 11/494,387

(22) Filed: Jul. 26, 2006

(65) Prior Publication Data

US 2007/0027445 A1    Feb. 1, 2007

Related U.S. Application Data

(63) Continuation of application No. 10/764,148, filed on Jan. 23, 2004, now Pat. No. 7,311,701.

(60) Provisional application No. 60/477,532, filed on Jun. 10, 2003.

(51) Int. Cl.
| | | |
|---|---|---|
| *A61B 18/14* | (2006.01) | |
| *A61N 7/02* | (2006.01) | |
| *A61B 8/12* | (2006.01) | |
| *A61B 8/00* | (2006.01) | |

(Continued)

(52) U.S. Cl.
    CPC ... *A61N 7/02* (2013.01); *A61B 8/12* (2013.01); *A61B 8/4488* (2013.01); *A61B 8/0883* (2013.01); *A61B 2017/00243* (2013.01); *A61B 2018/00351* (2013.01); *A61B 2019/5278* (2013.01); *A61N 2007/0078* (2013.01)

(58) Field of Classification Search
    CPC ...... A61B 8/12; A61B 8/4488; A61B 8/0883; A61B 18/14; A61B 2019/5278; A61B 2018/00351; A61B 2018/0057; A61B 2017/00243; A61N 7/02; A61N 2007/0078
    USPC ..................................................... 606/27, 41
    See application file for complete search history.

(56) References Cited

U.S. PATENT DOCUMENTS

| | | |
|---|---|---|
| 3,874,388 A | 4/1975 | King et al. |
| 4,788,975 A | 12/1988 | Shturman et al. |

(Continued)

FOREIGN PATENT DOCUMENTS

| | | |
|---|---|---|
| FR | 2827149 A | 1/2003 |
| GB | 2267035 A | 11/1993 |

(Continued)

OTHER PUBLICATIONS

Athraman et al., "Selective Photothermal Tissue Interaction Using 805-nm Laser and Indocyanine Green in Tissue Welding," Journal of X-Ray Science and Technology, vol. 12, No. 2, pp. 117-126 (2004).

(Continued)

*Primary Examiner* — Michael Peffley
*Assistant Examiner* — Samantha Good
(74) *Attorney, Agent, or Firm* — Downs Rachlin Martin PLLC

(57) ABSTRACT

Methods and apparatus are provided that enable a physician to image tissue within the body that is to be ablated, and then to ablate that tissue using a device having an ultrasound imaging system and an aligned high intensity focused ultrasound system.

16 Claims, 3 Drawing Sheets

(51) Int. Cl.
     *A61B 18/00*   (2006.01)
     *A61B 8/08*    (2006.01)
     *A61B 17/00*   (2006.01)
     *A61B 19/00*   (2006.01)
     *A61N 7/00*    (2006.01)

(56) References Cited

U.S. PATENT DOCUMENTS

| | | |
|---|---|---|
| 4,798,594 A | 1/1989 | Hillsted |
| 4,895,565 A | 1/1990 | Hillsted |
| 5,041,095 A | 8/1991 | Littrell |
| 5,292,362 A | 3/1994 | Bass et al. |
| 5,380,304 A | 1/1995 | Parker |
| 5,383,917 A | 1/1995 | Desai et al. |
| 5,391,140 A | 2/1995 | Schaetzle |
| 5,501,655 A * | 3/1996 | Rolt et al. ............ 601/3 |
| 5,620,481 A | 4/1997 | Desai et al. |
| 5,626,607 A | 5/1997 | Malecki et al. |
| 5,676,692 A * | 10/1997 | Sanghvi et al. ............ 607/98 |
| 5,693,078 A | 12/1997 | Desai et al. |
| 5,817,021 A | 10/1998 | Reichenberger |
| 5,895,356 A * | 4/1999 | Andrus et al. ............ 600/439 |
| 6,086,570 A | 7/2000 | Aboul-Hosen et al. |
| 6,211,335 B1 | 4/2001 | Owen et al. |
| 6,375,668 B1 | 4/2002 | Gifford et al. |
| 6,391,048 B1 | 5/2002 | Ginn et al. |
| 6,419,648 B1 * | 7/2002 | Vitek et al. ............ 601/3 |
| 6,423,057 B1 | 7/2002 | He et al. |
| 6,451,044 B1 * | 9/2002 | Naghavi et al. ............ 607/96 |
| 6,475,213 B1 | 11/2002 | Whayne et al. |
| 6,558,382 B2 | 5/2003 | Jahns et al. |
| 6,562,037 B2 | 5/2003 | Paton et al. |
| 6,595,934 B1 * | 7/2003 | Hissong et al. ............ 601/3 |
| 6,618,620 B1 * | 9/2003 | Freundlich et al. ............ 607/27 |
| 6,726,718 B1 | 4/2004 | Carlyle et al. |
| 6,733,498 B2 | 5/2004 | Paton et al. |
| 6,770,072 B1 | 8/2004 | Truckai et al. |
| 6,893,431 B2 | 5/2005 | Naimark et al. |
| 6,926,716 B2 | 8/2005 | Baker et al. |
| 6,929,644 B2 | 8/2005 | Truckai et al. |
| 6,932,812 B2 | 8/2005 | Crowley et al. |
| 6,946,134 B1 | 9/2005 | Rosen et al. |
| 7,025,756 B2 | 4/2006 | Frazier et al. |
| 7,151,964 B2 | 12/2006 | Desai et al. |
| 7,165,552 B2 | 1/2007 | Deem et al. |
| 7,311,701 B2 * | 12/2007 | Gifford et al. ............ 606/27 |
| 2001/0031922 A1 | 10/2001 | Weng et al. |
| 2001/0051803 A1 | 12/2001 | Desai et al. |
| 2002/0002371 A1 * | 1/2002 | Acker et al. ............ 606/27 |
| 2002/0032394 A1 * | 3/2002 | Brisken et al. ............ 601/2 |
| 2002/0065512 A1 * | 5/2002 | Fjield et al. ............ 606/27 |
| 2002/0156470 A1 * | 10/2002 | Shadduck ............ 606/41 |
| 2003/0014093 A1 | 1/2003 | Makin |
| 2003/0045901 A1 | 3/2003 | Opolski |
| 2004/0092973 A1 | 5/2004 | Chanduszko et al. |
| 2005/0075665 A1 | 4/2005 | Brenzel et al. |
| 2005/0125032 A1 | 6/2005 | Whisenant et al. |
| 2005/0171526 A1 | 8/2005 | Rioux et al. |
| 2005/0187568 A1 | 8/2005 | Klenk et al. |
| 2005/0192626 A1 | 9/2005 | Widomski et al. |
| 2005/0192627 A1 | 9/2005 | Whisenant et al. |
| 2005/0192654 A1 | 9/2005 | Chanduszko et al. |
| 2005/0209636 A1 | 9/2005 | Widomski et al. |
| 2005/0216054 A1 | 9/2005 | Widomski et al. |
| 2005/0251201 A1 | 11/2005 | Roue et al. |
| 2006/0052821 A1 | 3/2006 | Abbott et al. |
| 2006/0069408 A1 | 3/2006 | Kato |
| 2008/0058683 A1 * | 3/2008 | Gifford et al. ............ 601/3 |

FOREIGN PATENT DOCUMENTS

| | | |
|---|---|---|
| WO | WO 89/07909 | 9/1989 |
| WO | WO 99/23959 A1 | 5/1999 |
| WO | WO 01/13810 A1 | 3/2001 |
| WO | WO 01/45550 A2 | 6/2001 |
| WO | WO01/82778 * | 11/2001 |
| WO | WO 01/82778 A2 | 11/2001 |
| WO | WO 2005/046487 A1 | 5/2005 |
| WO | WO 2005/074814 A2 | 8/2005 |
| WO | WO 2005/115256 A2 | 12/2005 |

OTHER PUBLICATIONS

Fenner et al., "Shear Stregnth of Tissue Bonds as a Function of Bonding Temperature: A Proposed Mechanism for Laser-assisted Tissue Welding," Lasers in Medical Science, vol. 7, No. 1, pp. 39-43 (1992).

Godlewski et al., "Applications and Mechanisms of Laser Tissue Welding in 1995: Review," Proceedings of SPIE, vol. 2623 pp. 334-341 (Jan. 1996).

Olsen et al., "Developing an Animal Model for the Study of Fusion Using RF Energy," Proceedings of SPIE, vol. 5312, pp. 147-161 (Jul. 2004).

Ott et al., Comparative In Vitro Study of Tissue Welding Using a 808 nm Diode Laser and a Ho:YAG Laser, Lasers in Medical Science, vol. 16, No. 4, pp. 260-266 (Oct. 2001).

Poppas et al., "Temperature-Controlled Laser Photocoagulation of Soft Tissue: In Vivo Evaluation Using a Tissue Welding Model," Lasers in Surgery and Medicine, vol. 18, No. 4, pp. 335-344 (1996).

Stewart et al., "Laser Assisted Vascular Welding with Real Time Temperature Control," Lasers in Surgrey and Medicine, vol. 19, No. 1, pp. 9-16 (1996).

Tang et al., "Quantitave Changes in Collagen Levels Following 830-nm Diode Laser Welding," Lasers in Surgery and Medicine, vol. 22, No. 4, pp. 207-211 (1998).

Tang et al., "Morphologic Changes in Collagen Fibers after 830 nm Diode Laser Welding," vol. 21, No. 5 pp. 438-443 (1997).

* cited by examiner

METHODS AND APPARATUS FOR NON-INVASIVELY TREATING ATRIAL FIBRILLATION USING HIGH INTENSITY FOCUSED ULTRASOUND

REFERENCE TO RELATED APPLICATIONS

This application is a continuation of U.S. patent application Ser. No. 10/764,148, filed Jan. 23, 2004, now U.S. Pat. No. 7,311,701, which claims the benefit of U.S. provisional patent application Ser. No. 60/477,532, filed Jun. 10, 2003, the entireties of which are incorporated herein by reference.

FIELD OF THE INVENTION

The present invention relates to methods and apparatus for treatment of atrial fibrillation, and more particularly, to the use of high intensity focused ultrasound non-invasively to disrupt abnormal cardiac electrical pathways contributing to atrial fibrillation.

BACKGROUND OF THE INVENTION

Up until the 1980s, there was dramatic growth in the creation of new surgical methods for treating a wide variety of previously untreated conditions. Over the past twenty years there has been a clear trend towards the invention of devices and methods that enable less-invasive treatment of such diseases, moving from invasive surgery, and then to less-invasive surgery, and to interventional techniques. Ultimately, it is desirable to move to totally non-invasive therapies.

The history of treatment of atrial fibrillation has followed this progression. First, Dr. James Cox invented a new open-heart surgical procedure that interrupted depolarization waves using surgical incisions in the walls of the atrium. More recently, a number of devices have been developed to allow surgeons to make such lesions during surgery on the beating heart, and without making incisions in the walls of the atrium. More recently, interventional electrophysiologists have worked with companies to develop catheter-based systems to create similar lesions. Although only partial success has been achieved to date, there is optimism for further progress within the next few years.

Still more recently, concepts have been proposed for completely non-invasive treatment of atrial fibrillation by using focused external high-energy gamma or electron beam radiation to create lesions in specific areas of the atria of the heart. While offering great promise, these technologies also may present significant issues, including the type of lesion created in the atrial wall by radiation, difficulty in creating specific lesions and focusing on moving tissue, and the potential for damage to surrounding tissues. Such methods also require a preliminary computed tomography (CT) scan to program the computer that guides the energy beam.

A wide variety of energy modes have been used to create lesions using epicardial or intracardiac probes. Radio-frequency electrical energy, microwaves, cryothermia probes, alcohol injection, laser light, and ultrasound energy are just a few of the technologies that have been pursued.

Separately, several groups have developed focused ultrasound devices with both imaging and therapeutic capabilities. These efforts began perhaps with lithotripsy, in which a high power focused ultrasound system developed by Dornier Medizintechnik, Germany, is used to break up kidney stones in the body. The kidney stones generally are located within the body at a significant depth from the skin. One ultrasound imaging system is used to aim the system at the kidney stones, and then a second, high energy ultrasound system delivers energy that breaks up the stones so they can be passed.

More recently, Therus Corp of Seattle, Wash., has developed a system to seal blood vessels after the vessels have been punctured to insert sheaths and catheters. The Therus system shrinks and seals femoral artery punctures at a depth of approximately 5 cm.

In addition, Timi-3 Systems, Inc., Santa Clara, Calif., has developed and is testing a trans-thoracic ultrasound energy delivery system to accelerate the thrombolysis process for patients suffering an acute myocardial infarction. This system delivers energy at a frequency intended to accelerate thrombolysis without damaging the myocardium or vasculature of the heart.

Epicor Medical, Inc. of Sunnyvale, Calif., has developed a localized high intensity focused ultrasound ("HIFU") device to create lesions in the atrial walls. The Epicor device is a hand-held intraoperative surgical device, and is configured to be held directly against the epicardium or outside wall of the heart. When energized, the device creates full-thickness lesions through the atrial wall of the heart, and has demonstrated that ultrasound energy may be safely and effectively used to create atrial lesions, despite presence of blood flow past the interior wall of the atrium.

In addition, Transurgical, Inc., Setauket, N.Y. has been actively developing HIFU devices. However, while the Epicor Medical devices are placed in close approximation against the outside of the heart, the Transurgical devices are directed to intravascular catheters for heating or ablating tissue in the heart and require that the catheter be brought into close approximation with the targeted tissue.

In view of the aforementioned limitations of previously-known devices and methods, it would be desirable to provide methods and apparatus for treating atrial fibrillation or other conduction defects or ablating tissue at a distance from that tissue, so that the procedure may be performed non-invasively.

It also would be desirable to provide methods and apparatus for treating atrial fibrillation by applying energy from outside the body or from organs, such as the esophagus, that are easily accessible via natural body openings.

SUMMARY OF THE INVENTION

In view of the foregoing, it is an object of the present invention to provide methods and apparatus for treating atrial fibrillation and other conduction defects by ablating tissue at a distance from that tissue, so that the procedure may be performed non-invasively.

It is another object of the present invention to provide methods and apparatus for treating cardiac dysfunction by applying energy from outside the body or from neighboring organs, such as the esophagus, that are easily accessible.

These and other objects of the present invention are accomplished by providing methods and apparatus that enable a physician to image tissue within the body that is to be heated or ablated, and then to heat or ablate that tissue using a completely or relatively non-invasive procedure, and with little or no anesthesia. Advantageously, the methods and apparatus of the present invention are expected to be cost-effective and time-efficient to perform compared to the previously-known surgical and interventional procedures.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

The present invention is directed to methods and apparatus for creating lesions in the walls of the heart in a completely non-invasive manner using high intensity focused ultrasound (HIFU). Previously-known HIFU systems, such as those being developed by Epicor Medical or Transurgical, require close approximation of the HIFU device to the target tissue. The methods and apparatus of the present invention overcome this drawback by providing systems that enable the creation of lesions in the heart wall from a greater distance.

Figure 1:
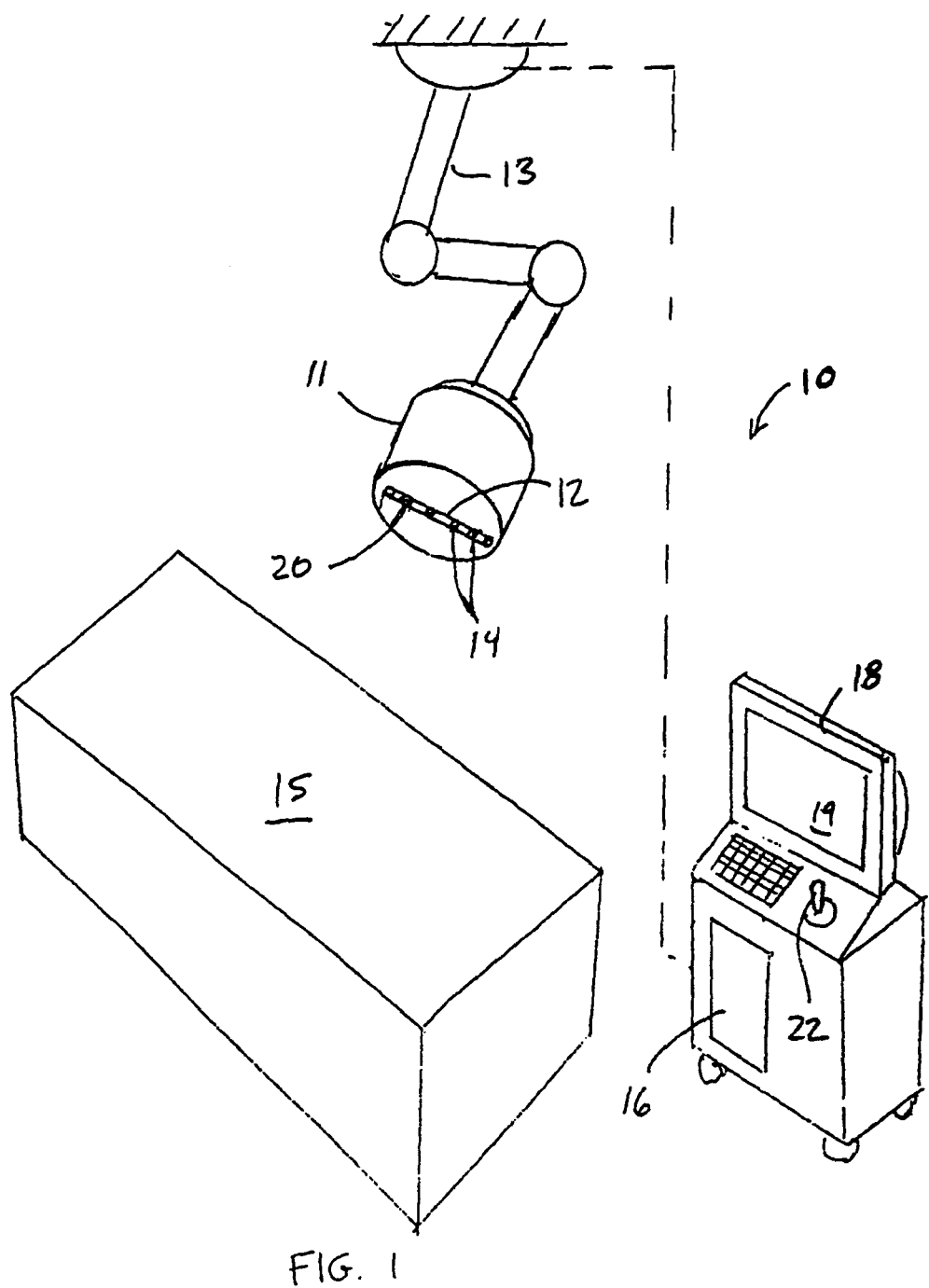
FIG. 1 is a schematic view of an illustrative imaging and treatment ultrasound sound system of the present invention.

Referring to FIG. 1, apparatus constructed in accordance with the principles of the present invention is described. System 10 comprises head 11 housing ultrasound imaging system 12 and high intensity focused ultrasound energy ("HIFU") system 14. Ultrasound imaging system 12 and HIFU system 14 may have in common all or just a subset of the transducers and related components, operating in different modes to image or ablate. Head 11 is mounted on arm 13 that permits the head to be positioned in contact with a patient (not shown) lying on table 15. Head 11 also may be a hand-held unit, not needing an arm 13 to support or position it. System 10 includes controller 16 that controls operation of imaging system 12 and HIFU system 14. Monitor 18 displays images output by imaging system 12 that allows the clinician to identify the desired locations on the walls of the heart to be treated.

Figure 2:
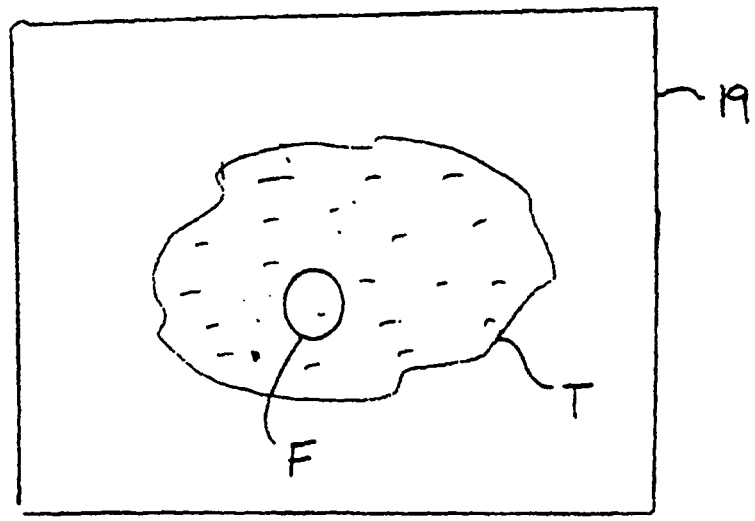
FIG. 2 is a schematic view of an illustrative display of the imaging and treatment ultrasound sound system of the present invention.

In accordance with the methods of the present invention, controller 16 and monitor 18 also are programmed to indicate the focus of the HIFU energy relative to the image of the tissue cross-section. FIG. 2 is illustrative screen display 19 of monitor 18 showing the outline T of the tissue, as imaged by imaging system 12, and a marker corresponding to the location of focal point F of HIFU system 14.

When activated, the HIFU system delivers ablative energy to the specific location shown on monitor 18 (focal point F in FIG. 2), thus enabling safe creation of transmural lesions. Because the HIFU system is configured to deliver energy from a number of sources focused towards the target tissue area, intervening tissue is subjected to only a fraction of the energy deposited in the target tissue receives, and thus the intervening tissue is not significantly heated or ablated.

Referring still to FIG. 1, ultrasound imaging system 12 may be similar in design to previously-known trans-thoracic ultrasound imaging systems, and are per se known. High intensity focused ultrasound system 14 may comprise one or more HIFU generators 20 constructed as described in U.S. Patent Publication No. US20010031922A1. As mentioned before, imaging system 12 and HIFU system 14 also may use common elements. Preferably, each HIFU generator 20 is the same as or is disposed approximately in the same plane as the imaging elements of ultrasound imaging system 12, so that the focus of HIFU system 14 occurs in the plane of the target tissue imaged by ultrasound imaging system 12. In addition, this arrangement advantageously ensures that the HIFU energy will reach the target.

In a preferred embodiment, HIFU generators 20 deliver energy at a frequency optimized for creating lesions in myocardium, to thereby interrupt conduction pathways through the tissue without reducing the strength of the tissue. Once the lesions are created, a gradual healing process is begun in which the lesions fibrose, but do not fall apart or regain the ability to conduct electrical impulses.

While it may be possible to image and heat simultaneously, it may occur that the output of HIFU system 14 may interfere with the ability to image the tissue using ultrasound imaging system 12. Accordingly, controller 16 may be programmed to time-gate operation of imaging system 12 and HIFU system 14, so that the tissue is alternately imaged and ablated at a frequency of up to several times per second.

In order to create linear lesions in the wall of the atria of the heart, it may be desirable to slowly move the focus of the HIFU system along the wall of the atrium during the ablation process. While this may be accomplished by manually moving the HIFU system, it may alternatively be desirable to automate the process, for example, for treating relatively short lesions that encircle each or all of the pulmonary veins. Controller 16 may include suitable programming and joystick 22, or other input device, for refocusing the focal point of HIFU system 14 along a desired trajectory.

Figure 3:
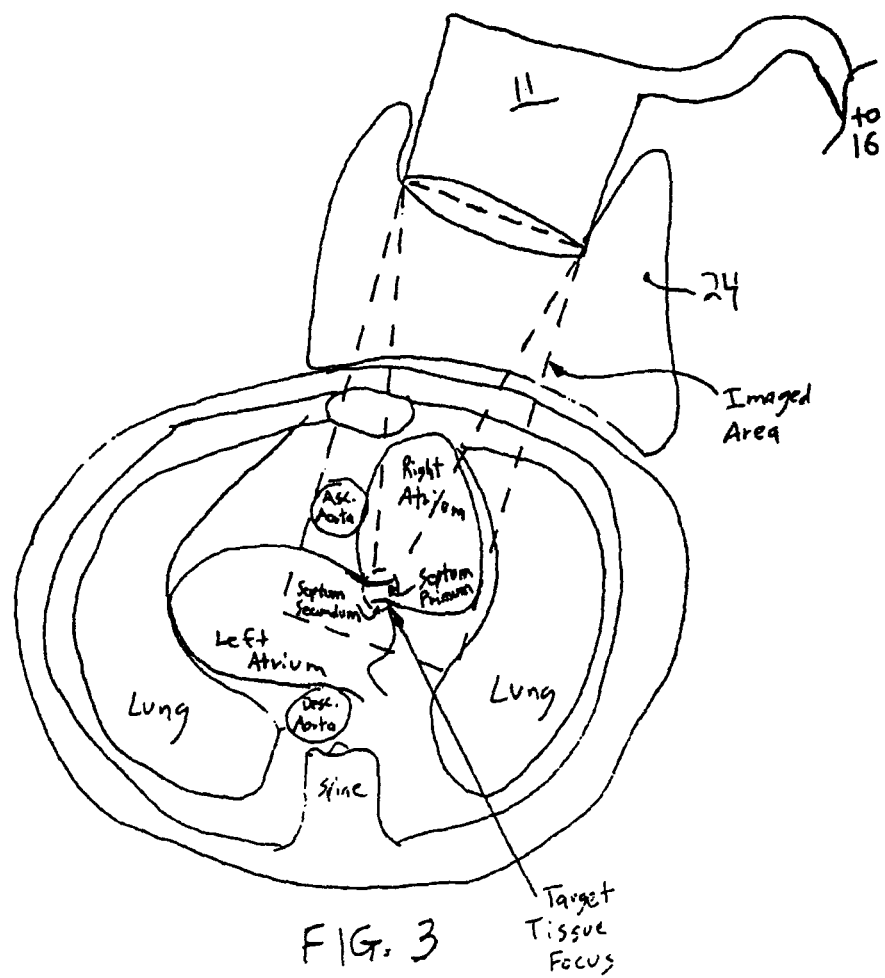
FIG. 3 is a schematic view showing the imaging and treatment ultrasound sound system of FIG. 1 disposed adjacent to a cross-section of a patient's thorax.

Referring now to FIG. 3, a further alternative for using HIFU system to create linear lesions is described. In the system shown in FIG. 3 the focus of the HIFU system is fixed at a certain point within the field of the ultrasound image. For example, the ultrasound image might show a picture of rectangular planar cross-section of tissue approximately 80 mm wide and 160 mm deep, with a fixed focus of the HIFU energy at a depth of 130 mm in the center of the field.

In operation, the clinician manually moves the probe until the desired tissue is in the target area, and then fires the HIFU system to ablate the tissue. With such a system the depth of maximal ablation is 130 mm below the skin. In order to ablate tissue located less than 130 mm below the skin and still retain a continuous fluid path from the probe to the target, the HIFU system includes fluid-filled balloon 24 that covers the face of the probe.

Balloon 24 preferably is filled with water and enables the clinician to reposition the probe at a variable distance from the skin. Balloon 24 also permits the clinician to position the probe at any desired angle to target tissue not aligned directly under the focal point of HIFU system 14. Alternatively, the patient could sit in a tub of water, so the patient's chest and the probe were both underwater, again ensuring a continuous fluid path.

As a further alternative, controller 16 may be programmed so that the depth of the focal point of the HIFU system is depth-adjustable relative to the imaged tissue. Advantageously, the depth of the targeted tissue could be adjusted relative to the imaged field, so a smaller fluid-filled balloon, or no balloon, is used to maintain fluid contact while adjusting the angle of the imaged section or make minor changes in the depth of the targeted tissue. WIPO Patent Publication No. WO 01/45550A2 to Therus describes several ways to adjust the depth of the focused energy by changing the radius of curvature of one or more of the ultrasound generators. Alternatively, the direction of several focused energy generators of relatively fixed focal length could be shifted relative to one another to move the focal point.

In accordance with the principles of the present invention, focused energy is applied from outside the patient's body.

Because ultrasound energy does not travel coherently through non-fluid filled tissue, such as the lungs, positioning of the ultrasound imaging system and HIFU system at certain angles may be more advantageous for treatment of specific areas of the heart. For example, the posterior wall of the left atrium is a particularly important treatment area for treating atrial fibrillation; it is also a peculiarly difficult area to image with trans-thoracic ultrasound.

Accordingly, it may be desirable to locate the imaging system and HIFU system on a movable arm so as to permit other external approaches, such as from below the diaphragm on the left anterior side of the body, so the ultrasound has a coherent path through the diaphragm and apex and ventricles of the heart to the atria. Application of the probe to a patient's back also may provide a coherent path to the posterior wall of the patient's left atrium.

It is expected that the system and methods of the present invention also may be useful for treating a number of cardiac dysfunctions. Apart from treatment of atrial fibrillation, the methods and apparatus of the present invention also may be used to treat other electrophysiologic defects of the heart, or to create lesions for other purposes. For example, if transmyocardial revascularization (TMR) is believed to have a positive effect on damaged ventricles by causing focal areas of damage and healing, such lesions may be created non-invasively using the present invention.

As another example, localized tissue damage and the consequent healing process may cause the septum primum and septum secundum of a patent foramen ovale (PFO) to heal together, closing the PFO. If the system and methods of present invention are effective in closing PFO even a small percentage of the time, the non-invasive nature of the procedure might have it the first choice for use an initial therapy in most cases.

In addition, the HIFU system described hereinabove also may be used to repair diseased heart valves, by shrinking tissue in certain areas. For example, specific areas of elongated chordae of a mitral valve leaflet may be shortened by heating using the external HIFU of the present invention.

While in the preferred embodiment described hereinabove energy is delivered from outside the body, situations may arise where it is difficult to deliver the energy to locations deep inside the body or locations adjacent to the lungs or other non-ultrasound-conductive tissue.

Figure 4:
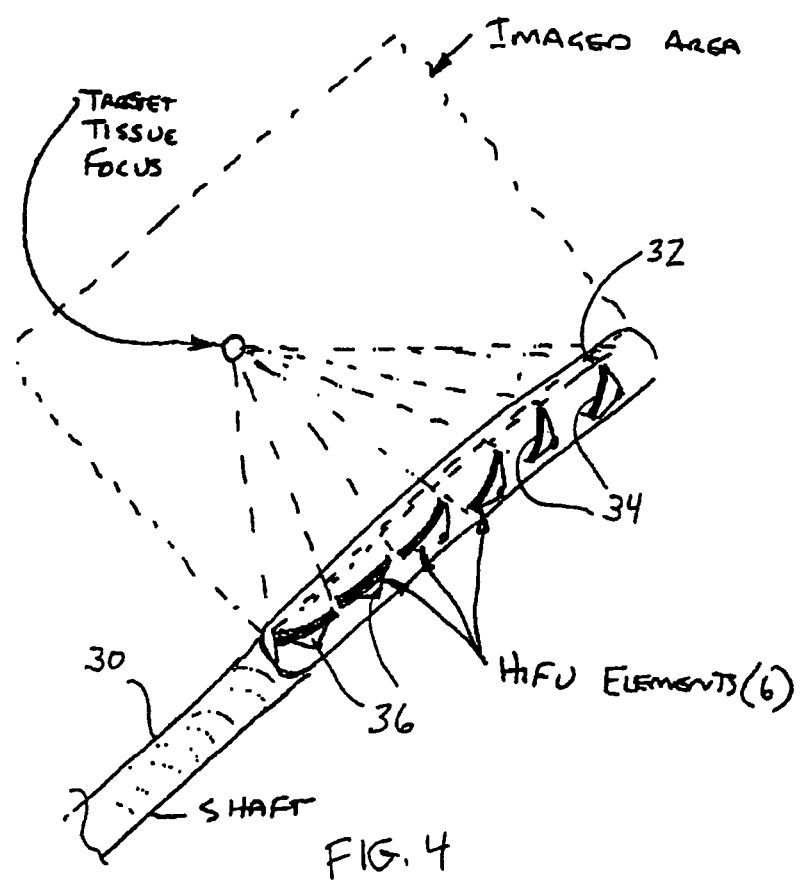
FIG. 4 is a schematic view of the distal region of a catheter-based high intensity focused ultrasound array.

Referring now to FIG. 4, and in accordance with another aspect of the present invention, methods and apparatus are provided for positioning a probe inside the body and closer to the targeted tissue, but still not necessarily adjacent to it. Intraluminal probe 30 is configured to deliver HIFU energy to the heart from the esophagus, from the aorta, or from the great veins of the heart such as the inferior vena cava, superior vena cava, or the right atrium itself.

This approach is fundamentally different from previously-known methods of performing ablation during surgical procedures using epicardial probes or during interventional procedures using intracardiac ablation catheters. These previously-known devices are designed to be in direct contact or at least very close proximity (e.g., within 5 mm) of the target tissue, and are not designed to avoid ablating intervening tissue between the probe and the target tissue.

In addition, previously-known devices are capable of making only a single lesion from a given position, rather than forming a number of lesions at a distance from a device from a single location. Making multiple lesions from a single catheter position advantageously may save time and reduce the cost of the procedure. For example, approximating a surgical maze procedure using previously-known intracardiac catheters typically takes from four to eight hours, and subject both the patient and physician to high levels of radiation from the fluoroscope. By contrast, a device constructed in accordance with the principles of the present invention, under ultrasound imaging guidance, could create multiple lesions while disposed at a single position in the esophagus, aorta, or great veins or right atrium.

Still referring to FIG. 4, intraluminal catheter 30 is designed to image and deliver HIFU energy from body lumens such as the esophagus, aorta, and great veins. Catheter 30 preferably has a diameter in a range of 5 to 10 mm for vascular devices, and a diameter in a range of 5 to 20 mm for an esophageal device. Imaging elements 32 and HIFU elements 34 are arranged linearly along the longitudinal axis of the catheter.

The linear nature of the imaging element and HIFU element array may impose limitations on the ability to reposition the device. While translation and rotation of the catheter may be relatively easy, it is contemplated that it may be difficult to move the device very far to one side or another within a relatively small-diameter body lumen.

Accordingly, intraluminal catheter 30 preferably is configured to adjust the focal point of the HIFU system with respect to both longitudinal position and depth. This may be accomplished by programming the controller used with intraluminal catheter 30 to adjust the focal point of the HIFU system, as described above. Alternatively, refocusing of the array of HIFU elements may be achieved by locating individual HIFU elements on independently steerable actuators 36. Actuators 36 are controlled by the system controller and permit the clinician to move the focal point of the HIFU array to any desired point in the field of view of the imaging system.

In accordance with another aspect of the present invention, methods of using intraluminal catheter 30 to heat or ablate from the esophagus to treat atrial fibrillation are described. The esophagus is separated from the center of the posterior left atrial wall only by the oblique pericardial sinus, so a linear vertical lesion may be easily made in the center of the posterior left atrial wall using a probe capable of delivering energy at a distance of approximately 5-10 mm.

Such methods are believed to offer substantial advantages with respect to ease of use, and may be effective in treating a high percentage of atrial fibrillation patients. These methods also may obviate the need to contract significant areas of the posterior wall of the left atrium, as typically happens when broad encircling lesions are made around the pulmonary veins.

In accordance with this aspect of the present invention, one or more vertical ablation lines are formed in the posterior wall of the left atrium using intraluminal catheter 30 disposed within the esophagus. It is expected that formation of straight ablation lines vertically in the posterior wall of the atrium, under ultrasound imaging guidance from the esophagus, may also be easier than making encircling ablation lines around the pulmonary veins.

The foregoing methods of creating lesions are consistent with the underlying concept of the maze procedure as invented by Dr. James Cox in the early 1990s. His research in mapping the depolarization waves in patients with atrial fibrillation showed that dysfunction arose from waves recirculating around the atria. This recirculation is enabled by slightly damaged tissue, which slows the progress of the depolarization wave, and enlargement of the atria due to damage, valve dysfunction, or congestive heart failure.

The maze concept relies on the creation of numerous dead-end pathways in the atria, so the depolarization wave reaches all of the atrial walls, but cannot recirculate. A series of vertical ablation lines in the posterior wall of the left atrium, extending from the atrioventricular groove up to above the superior pulmonary veins would accomplish exactly this goal.

Preferably, the ablation lines extend all the way down to the atrioventricular groove. This allows the depolarization wave to reach that tissue from the dome of the left atrium (the more cranial and anterior surface) but not to progress back to the rest of the atrial wall along the atrioventricular groove.

As described above, intraluminal catheter 30 preferably is configured, either mechanically or by suitable software algorithms, to move its focal point longitudinally to enable a continuous linear ablation without moving the device. Alternatively, the HIFU array of the catheter may be configured to create a linear ablation, or have a fixed-focus so that a linear ablation may be created by translating the HIFU array within the esophagus.

Further in accordance with the present invention, additional lesions may be made closer to the left and right pulmonary veins. More preferably, lesions could be made on the opposite sides of the left and right pulmonary veins, i.e., to the left of the left pulmonary veins and to the right of the right pulmonary veins. Alternatively, and depending on the geometry of the HIFU probe, it may be more desirable to make encircling lesions in the left and right pulmonary veins using the same vertical motion.

In addition, it may be beneficial to cool tissue surrounding the HIFU array of intraluminal catheter 30, to reduce the risk of damage to the esophagus. Intraluminal catheter 30 may therefore include a water jacket that circulates fluid around the HIFU array to prevent any heat generated by the array or ultrasound energy absorbed by the esophagus from causing any tissue damage.

The methods and apparatus of the present invention also may be beneficially applied to other applications besides cardiac dysfunction. For example, the apparatus of the present invention may be used, disposed in small body lumens, nearly anywhere a radiofrequency ablation probe is currently being used to ablate or shrink tissue. Such treatments include treating the prostate from the urethra, tightening up the bladder neck from inside the vagina, ablating fibroid masses from inside the uterus, tightening up the tissue in the area of the gastroesophageal junction, and so on. Likewise, the external device described with respect to FIG. 1 may be beneficially used to ablate tumors almost anywhere in the body that is accessible to focused ultrasound.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. A method of non-invasively treating atrial fibrillation in a heart of a patient, the method comprising:
    providing a housing having an ultrasound imaging system and a high intensity focused ultrasound system disposed in alignment with the ultrasound imaging system;
    inserting the housing into a body lumen of the patient with the housing located at a treatment location spaced from a target site on a posterior wall of the heart at which a lesion is to be formed to interrupt electrical conduction in the posterior wall so as to treat atrial fibrillation, wherein said inserting the housing into the body lumen includes inserting the housing into the patient's esophagus so that the treatment location is in the esophagus;
    operating the ultrasound imaging system to generate an image of a portion of the heart containing the target site; and
    while the housing is located at the treatment location, operating the high intensity focused ultrasound system, guided by the image, to ablate cardiac tissue at the target site so as to interrupt electrical-conduction pathways on the posterior wall of the heart, while patient tissue intervening between the housing and the cardiac tissue is not ablated.

2. The method of claim 1 further comprising generating and displaying a marker corresponding to a focal point of the high intensity focused ultrasound system on the image.

3. The method of claim 1 further comprising modifying a location of the target site by adjusting a location of a focal point of the high intensity focused ultrasound system.

4. The method of claim 1 wherein the treatment location is more than 5 mm from the target site.

5. The method of claim 1 wherein the ultrasound imaging system comprises an array of imaging elements and the high intensity focused ultrasound system comprises an array of HIFU elements, wherein at least one of the imaging elements is not used as a HIFU element.

6. The method of claim 1 wherein the housing is positioned at the treatment location without the use of anesthesia.

7. The method of claim 1 wherein the high intensity ultrasound system is operated to create at least one of linear lesions and encircling lesions at the target site.

8. The method of claim 1 wherein a focal point of the high intensity ultrasound system is moved along a desired trajectory on the posterior wall of the heart while the high intensity ultrasound system is operating to create a continuous linear lesion.

9. The method of claim 8 wherein the focal point is moved without moving the housing.

10. The method of claim 1 wherein the high intensity ultrasound system comprises a plurality of HIFU elements each mounted to a separate steerable actuator, and wherein the actuators are steered to move a focal point of the high intensity ultrasound system along a desired trajectory while the high intensity ultrasound system is operating.

11. The method of claim 1 wherein the posterior wall of the heart is the left atrial wall.

12. The method of claim 1, wherein said operating the high intensity focused ultrasound system consists essentially of operating the high intensity focused ultrasound system so as to form one or more vertical ablation lines in the posterior wall of the left atrium.

13. The method of claim 1, further comprising, during said operating the high intensity focused ultrasound system, flowing, within a water jacket, a fluid around the high intensity focused ultrasound system to remove heat generated by the high intensity focused ultrasound system so as to inhibit damaging esophageal tissue.

14. A method of non-invasively treating atrial fibrillation in a heart of a patient, the method comprising:
    providing a housing configured and dimensioned for placement in the patient's esophagus with an ultrasound imaging system and a high intensity focused ultrasound system disposed in alignment with the ultrasound imaging system disposed within the housing;
    inserting the housing into the esophagus, with the housing located at a treatment location spaced from a target site on a posterior wall of the heart;
    operating the ultrasound imaging system to generate an image of a portion of the posterior wall of the heart containing the target site;

forming a lesion with the high intensity focused ultrasound system in the posterior wall of the heart at the target site to interrupt electrical conduction pathways in the posterior wall, while patient tissue including the esophageal wall intervening between the housing and the posterior wall of the heart is not ablated; and guiding said lesion forming with said image during said forming.

15. The method of claim 14, further comprising protecting the esophageal wall and tissue intervening between the housing and the posterior wall of the heart.

16. The method of claim 15, wherein said protecting comprises circulating fluid around the high intensity focused ultrasound system to prevent tissue damage.

* * * * *